(12) United States Patent
Galvez

(10) Patent No.: US 7,731,995 B2
(45) Date of Patent: Jun. 8, 2010

(54) METHODS FOR USING SOY PEPTIDES TO INHIBIT H3 ACETYLATION, REDUCE EXPRESSION OF HMG COA REDUCTASE, AND INCREASE LDL RECEPTOR AND SP1 EXPRESSION IN A MAMMAL

(76) Inventor: Alfredo Flores Galvez, 3500 Squew Rd., West Sacramento, CA (US) 95691

( * ) Notice: Subject to any disclaimer, the term of this patent is extended or adjusted under 35 U.S.C. 154(b) by 768 days.

(21) Appl. No.: 11/532,528

(22) Filed: Sep. 16, 2006

(65) Prior Publication Data

US 2008/0070827 A1 Mar. 20, 2008

(51) Int. Cl.
A61K 36/48 (2006.01)
A62K 38/00 (2006.01)
A61K 51/00 (2006.01)
C07K 5/00 (2006.01)
C07K 7/00 (2006.01)
C07K 16/00 (2006.01)
C07K 17/00 (2006.01)

(52) U.S. Cl. .......................... 424/757; 530/324; 514/2; 424/1.69

(58) Field of Classification Search ........................ None
See application file for complete search history.

(56) References Cited

U.S. PATENT DOCUMENTS

| | | | |
|---|---|---|---|
| 6,107,287 | A | 8/2000 | de Lumen et al. |
| 6,391,848 | B1 * | 5/2002 | de Lumen et al. ............... 514/2 |
| 6,544,956 | B1 | 4/2003 | de Lumen et al. |
| 7,375,092 | B2 | 5/2008 | De Lumen et al. |
| 7,404,973 | B2 | 7/2008 | Konwinski et al. |
| 2003/0027765 | A1 * | 2/2003 | Galvez ......................... 514/12 |
| 2003/0064121 | A1 | 4/2003 | Konwinski et al. |
| 2003/0229038 | A1 | 12/2003 | de Lumen et al. |
| 2007/0054031 | A1 | 3/2007 | Liu |

FOREIGN PATENT DOCUMENTS

| | | |
|---|---|---|
| EP | 1017796 B1 | 5/2005 |
| WO | WO 99/15842 | 4/1999 |
| WO | 00/66625 | 9/2000 |
| WO | 01/072784 | 4/2001 |
| WO | 01/34808 A2 | 5/2001 |
| WO | WO 03/007976 A1 | 1/2003 |

OTHER PUBLICATIONS

Galvez, Alfredo F., et al., Chemopreventive Property of a Soybean Peptide (lunasin) That Binds to Deacetylated Histones and Inhibits Acetylation, Cancer Research (Oct. 15, 2001) 51, 7473-7478, USA.
Galvez, Alfredo F., Et Al., In Vitro and In Vivo Chemopreventive Properties of a Soybean Peptide (Lunasin) That Binds to Deacetylated histones and Inhibits Acetylation, American Society for Nutritional Sciences J. Nutr. 132:558S-619S, 2002, USA.
Jeong, Hyung J., et al., Barley Lunasin Suppresses Ras-induced Colony Formation and Inhibits Core Histone Acetylation in Mammalian Cells, J. Agric. Food Chem. (Oct. 9, 2002) 50(21): 5903-8, USA.
Park, Jae H., et al., Contents and Bioactivities of Lunasin, Bowman-Birk Inhibitor, and Isoflavones in Soybean Seed, J. Agric. Food Chem. (2005) 53, 7686-7690, USA.
Jeong, Hyung J., et al., Characterization of Lunasin Isolated from Soybean, J. Agric. Food Chem. (2003) 51, 7901-7906, USA.

* cited by examiner

*Primary Examiner*—Maury Audet
(74) *Attorney, Agent, or Firm*—Kathryn P. Wilke

(57) ABSTRACT

Controlled studies demonstrate that methods using soy related peptides inhibit H3 acetylation, reduce expression of HMG CoA reductase and increase LDL receptor and Sp1 expression in mammals. The present disclosure is generally directed to using lunasin peptides and/or lunasin peptide derivatives to 1) inhibit H3 acetylation, 2) reduce expression of HMG CoA reductase, 3) increase LDL receptor expression or 4) increase Sp1 expression in a mammal. In at least one exemplary embodiment of the present disclosure, an effective amount of lunasin peptides or lunasin peptide derivatives and one or more enzyme inhibitors is provided to a mammal to 1) inhibit H3 acetylation, 2) reduce expression of HMG CoA reductase, 3) increase LDL receptor expression or 4) increase Sp1 expression in a mammal.

16 Claims, 6 Drawing Sheets

Fig. 1

2S Albumin Protein Containing Lunasin Subunit

Signal Peptide        Small subunit (Lunasin)

MTKFTLLLSLLFCIAHTCSASKWQHQQDSCRKQLQGVNL

Chromatin-targeting   Cell adhesion
  motif                 motif         Poly-aspartyl end     Linker

TPCEKHIMEKIQGRGDDDDDDDDNHILRTMGGRINYI

Large Subunit (methionine-rich protein)

RRNEGKDEDEEEGHMQKCCTEMSELRSPKCQCKALQKI

Nuclear localization
                  sequence

MENQSEELEEKQKKKMEKELINLAIMCRFGPMIQCDLSS
DD

The 2S albumin protein encoded by Gm2S-1 cDNA.

HMG CoA-Reductase Expression In Lunasin-Treated Cholesterol-Free Media

LDL Receptor Expression In Lunasin-Treated Cholesterol-Free Media

Sp1 Expression In Lunasin Treated Growth Media And Cholesterol Free Media

Western Blots From Experiments On PCAF Reaction Products Demonstrating
That Lunasin Caused A Dramatic Reduction In Histone H3 Acetylation Western Blots From Experiments On PCAF HAT Reaction Products Demonstrating That Lunasin Caused A Dramatic Reduction In Histone H3 Acetylation

SEQUENCE LISTING

<160> NUMBER OF SEQ ID NOS: 2

<210> SEQ ID NO 1
<211> LENGTH: 157
<212> TYPE: PRT
<213> ORGANISM: Soybean

<400> SEQUENCE: 1

Met Thr Lys Phe Thr Ile Leu Leu Ile Ser Leu Leu Phe Cys Ile Ala
1               5                   10                  15

His Thr Cys Ser Ala Ser Lys Trp Gln His Gln Gln Asp Ser Cys Arg
            20                  25                  30

Lys Gln Leu Gln Gly Val Asn Leu Thr Pro Cys Glu Lys His Ile Met
        35                  40                  45

Glu Lys Ile Gln Gly Arg Gly Asp Asp Asp Asp Asp Asp Asp Asp
    50                  55                  60

Asn His Ile Leu Arg Thr Met Gly Gly Arg Ile Asn Tyr Ile Arg Arg
65                  70                  75                  80

Asn Glu Gly Lys Asp Glu Asp Glu Glu Glu Gly His Met Gln Lys Cys
                85                  90                  95

Cys Thr Glu Met Ser Glu Leu Arg Ser Pro Lys Cys Gln Cys Lys Ala
                100                 105                 110

Leu Gln Lys Ile Met Glu Asn Gln Ser Glu Glu Leu Glu Glu Lys Gln
            115                 120                 125

Lys Lys Lys Met Glu Lys Glu Leu Ile Asn Leu Ala Thr Met Cys Arg
        130                 135                 140

Phe Gly Pro Met Ile Gln Cys Asp Leu Ser Ser Asp Asp
145                 150                 155

<210> SEQ ID NO 2
<211> LENGTH: 43
<212> TYPE: PRT
<213> ORGANISM: Soybean

<400> SEQUENCE: 2

Ser Lys Trp Gln His Gln Gln Asp Ser Cys Arg Lys Gln Leu Gln Gly
1               5                   10                  15

Val Asn Leu Thr Pro Cys Glu Lys His Ile Met Glu Lys Ile Gln Gly
            20                  25                  30

Arg Gly Asp Asp Asp Asp Asp Asp Asp Asp Asp
        35                  40

US 7,731,995 B2

METHODS FOR USING SOY PEPTIDES TO INHIBIT H3 ACETYLATION, REDUCE EXPRESSION OF HMG COA REDUCTASE, AND INCREASE LDL RECEPTOR AND SP1 EXPRESSION IN A MAMMAL

RELATED APPLICATION

This application is related to U.S. application Ser. No. 11/532,526, filed concurrently on Sep. 16, 2006, the contents of which are incorporated by reference herein in its entirety.

BACKGROUND

1. Field of the Invention

This disclosure relates generally to a class of peptides that provide mammals with a variety of health related benefits. More specifically, the present disclosure related to using soy peptides to inhibit H3 acetylation, reduce expression of HMG CoA reductase and increase LDL receptor and Sp1 expression in a mammal.

2. Background of the Invention

Being able to control or manipulate certain important biological processes provides numerous benefits to researchers and individuals alike. The ability to effect expression of important receptors, enzymes and activators allows researchers to better understand complex biological mechanisms and create novel and beneficial therapies. For example, H3 acetylation, expression of HMG CoA reductase and LDL receptor and Sp1 expression in mammals pays a significant role in various health related factors, including but not limited to total and cholesterol levels and cancer prevention. Accordingly, manipulation and control of these biological mechanisms or factors would provide numerous health related benefits and allow researches with new avenues to develop new therapies. Unfortunately, presently there are no known effective methods of safely inhibiting H3 acetylation, reducing expression of HMG CoA reductase and increasing LDL receptor and Sp1 expression in a mammal. The ability to influence these and other biological factors, would be very beneficial to the fields of science and medicine. Accordingly, there exists a need for improved methods of inhibiting H3 acetylation, reducing expression of HMG CoA reductase and increasing LDL receptor and Sp1 expression in a mammal. The present invention provides these and other related benefits.

SUMMARY OF THE INVENTION

The present invention relates generally to a class of peptides that provide mammals with a variety of health related benefits. More specifically, the present invention involves to using soy peptides to inhibit H3 acetylation, reduce expression of HMG CoA reductase and increase LDL receptor and Sp1 expression in a mammal.

In at least one exemplary embodiment of the present invention, a method of inhibiting H3 acetylation in a mammal is provided. The method includes providing an effective amount of lunasin peptides to a mammal to inhibit H3 acetylation in the mammal.

In at least one other exemplary embodiment of the present invention, a method of reducing expression of HMG CoA reductase in a mammal is provided. The method includes providing an effective amount of lunasin peptides to a mammal to reduce expression of HMG CoA reductase in the mammal.

In at least one other exemplary embodiment of the present invention, a method of increasing LDL receptor expression in a mammal is provided. The method includes providing an effective amount of lunasin peptides to a mammal to increase LDL receptor expression in the mammal.

In at least one other exemplary embodiment of the present invention, a method of increasing Sp1 transcriptional activator expression in a mammal is provided. The method includes providing an effective amount of lunasin peptides to a mammal to increase Sp1 transcriptional activator expression in the mammal.

In one aspect of at least on embodiment of the present invention, the effective amount of lunasin peptides that inhibit H3 acetylation, reduce expression of HMG CoA reductase, increase LDL receptor expression or increases Sp1 transcriptional activator expression in a mammal is 25 to 100 mgs daily.

In another aspect of at least on embodiment of the present invention, the lunasin peptides include lunasin peptides or lunasin peptide derivatives.

In yet another aspect of at least on embodiment of the present invention, the lunasin peptides are obtained from, soy, seed bearing plants other than soy, using recombinant DNA techniques and synthetic polypeptide production or any combination thereof.

In yet another aspect of at least one embodiment of the present invention, the method includes providing an effective amount of one or more protease enzyme inhibitors with or without the lunasin peptides.

DRAWINGS

The above-mentioned features and objects of the present disclosure will become more apparent with reference to the following description taken in conjunction with the accompanying drawings wherein like reference numerals denote like elements and in which:

FIG. 1 shows the 2S albumin protein encoded by Gm2S 1 cDNA (SEQ ID NO 1). Arrows indicate endoproteolytic sites that give rise to small subunit (lunasin) (SEQ ID NO 2) and the large subunit (methionine rich protein). Important regions in both subunits are indicated.

DETAILED DESCRIPTION

Figure 2:
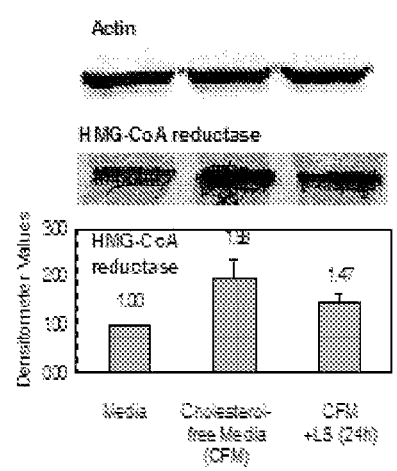
FIG. 2 shows the results of experiments measuring HMG CoA reductase expression when cholesterol free media is treated with lunasin.

Lunasin (a.k.a. lunastatin) is a recently discovered bioactive component in soy with a novel chromatin-binding property and epigenetic effects on gene expression (17, 18). The lunasin soy peptide is heat stable, water soluble and found in significant amounts in select soy protein preparations (19). Studies show that it can get inside mammalian epithelial cells through its RGD cell adhesion motif, bind preferentially to deacetylated histones and inhibit histone H3 and H4 acetylation (20). There is growing evidence that cellular transformation, responses to hormones and dietary and environmental effects involve epigenetic changes in gene expression, which are modulated by the reversible processes of DNA methylation-demethylation and histone acetylation-deacetylation (21, 22). Lunasin is the first natural substance to be identified as a histone acetylase inhibitor, although it does not directly affect the histone acetylase enzyme. It inhibits H3 and H4 acetylation by binding to specific deacetylated lysine residues in the N-terminal tail of histones H3 and H4, making them unavailable as substrates for histone acetylation. The elucidation of the mechanism of action makes lunasin an important molecule for research studies to understand the emerging role of epigenetics and chromatin modifications in important biological processes.

The study on the effect of lunasin on prostate carcinogenesis at the University of California at Davis revealed the effects of lunasin on histone H4 modifications and the up regulation of chemopreventive genes, (23). However, until now, the specific effect of lunasin binding to deacetylated H3 N-terminal tail and the inhibition of H3 histone acetylation in biological systems had not yet been investigated. To determine the specific biological effect of lunasin binding to deacetylated histone H3 and inhibition of acetylation, the induction of genes involved in cholesterol biosynthesis by the sterol regulatory element binding proteins (SREBP) was chosen as a biological model. This biological model was chosen because activation of SREBPs by sterol depletion results in the increased acetylation of histone H3 but not histone H4, by the histone acetylase enzyme PCAF, in chromatin proximal to the promoters of HMG CoA reductase and the LDL receptor genes (24) and SREBP activation results in the increased recruitment of co-regulatory factors, CREB to the promoter of HMG CoA reductase gene, and Sp1 to the promoter of LDL receptor gene (24).

Our studies on in vitro histone acetylase (HAT) assays show that lunasin significantly inhibits histone H3 acetylation (specifically lysine 14 in H3 N-terminal tail) by the histone acetylase enzyme, PCAF. Cell culture experiments using HepG2 liver cells show that synthetic lunasin can significantly reduce HMG CoA reductase expression and increase LDL receptor gene expression in cholesterol-free media similar to the effects of statin (cholesterol-lowering) drugs. Our studies have also shown that the increase in LDL receptor expression coincides with the increase in Sp1 expression in cholesterol-free media. Based on these studies, a molecular mechanism of action is proposed wherein synthetic lunasin reduces total and LDL cholesterol levels by binding to deacetylated histone H3 and inhibiting histone H3 acetylation by PCAF (through its association with the CREB-binding protein), thereby reducing SREBP activation of the HMG CoA reductase gene resulting in lower endogenous cholesterol biosynthesis, and by increasing the expression of the Sp1 co-activator in sterol-free media and upon SREBP activation, higher amount of membrane bound LDL receptors is expressed leading to significant reduction of plasma LDL cholesterol levels (25).

Our data described and shown below demonstrates that lunasin (a.k.a. lunastantin) is the bioactive agent from soy responsible for inhibiting H3 acetylation, reducing expression of HMG CoA reductase and increasing LDL receptor and Sp1 expression in a mammal.

Our surprising finding that lunasin inhibit H3 acetylation, reduce expression of HMG CoA reductase and increase LDL receptor and Sp1 expression in a mammal can be used for numerous health related benefits, including but not limited to, to lower total or LDL cholesterol levels or to prevent, control or treat cancers in mammals. These effects of lunasin can be further increased by developing formulations of lunasin and lunasin derivatives that are optimized for adsorption and delivery to the liver.

Lunasin is the small subunit peptide of a cotyledon-specific 2S albumin. FIG. 1 shows the 2S albumin protein and the small lunasin subunit. It has been shown that constitutive expression of the lunasin gene in mammalian cells disturbs kinetochore formation and disrupts mitosis, leading to cell death (18). When applied exogenously in mammalian cell culture, the lunasin peptide suppresses transformation of normal cells to cancerous foci that are induced by chemical carcinogens and oncogenes. To elucidate its chemopreventive mechanism of action, we have shown that lunasin (a) is internalized through its RGD cell adhesion motif, (b) colocalizes with hypoacetylated chromatin in telomeres at prometaphase, (c) binds preferentially to deacetylated histone H4, which is facilitated by the presence of a structurally conserved helical motif found in other chromatin-binding proteins, (d) inhibits histone H3 and H4 acetylation, and (e) induces apoptosis in E1A-transfected cells (20). Based on these results, a novel chemopreventive mechanism has been proposed wherein lunasin gets inside the nucleus, binds to deacetylated histones, prevents their acetylation and inhibits gene expression like those controlled by the Rb tumor suppressor and h-ras oncogene.

Lunasin Reduces Expression of HMG-CoA Reductase, Increases Expression of LDL Receptor The lowering of serum cholesterol by statin drugs is achieved by competitively inhibiting the HMG-CoA reductase, the rate limiting enzyme in the body's metabolic pathway for synthesis of cholesterol. By reducing endogenous cholesterol synthesis, statins also cause liver cells to up regulate expression of the LDL receptor, leading to increased clearance of low-density lipoprotein (LDL) from the bloodstream (25). In 1985, Michael Brown and Joseph Goldstein received the Nobel Prize in Medicine for their work in clarifying this LDL-lowering mechanism.

Transcriptional regulation of HMG-CoA reductase and LDL-receptor is controlled by the Sterol Regulatory Element-Binding Protein-1 and-2 (SREBP). This protein binds to the sterol regulatory element (SRE) located on the 5' end of the reductase and the LDL receptor genes. When SREBP is inactive, it is bound to the ER or nuclear membrane. When cholesterol levels fall, SREBP is released from the membrane by proteolysis and migrates to the nucleus, where it binds to the SRE to up regulate transcription of HMG CoA reductase and LDL receptor (24, 25).

Figure 3:
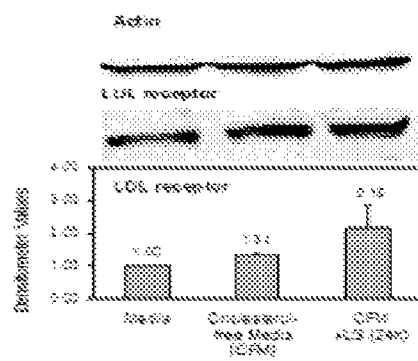
FIG. 3 shows the results of experiments measuring LDL receptor expression when cholesterol free media is treated with lunasin.

In cell culture of HepG2 liver cells, it is possible to activate SREBP and increase the expression of HMG CoA-reductase and LDL-receptor by removing cholesterol in the growth media. This can be achieved by exposing the cells to serum-free media for 24 h (31, 32). FIGS. 2 & 3 shows up regulation of HMG CoA reductase (98% increase) and LDL-receptor (34% increase) when HepG2 cells are grown in cholesterol-free media for 24 h. However when lunasin is added to the cholesterol-free media, the expression of the HMG CoA reductase is reduced by more than 50% (FIG. 2), while the expression of LDL-receptor has increased by more than 60% (FIG. 3). This effect of lunasin is similar to statin drugs that reduces endogenous cholesterol synthesis by inhibiting HMG CoA reductase activity, which leads to increased LDL receptor expression. However, the mode of action of lunasin differs from statin drugs in that it appears to inhibit expression of HMG CoA reductase at the transcriptional level, rather than on inhibiting its enzyme activity. Like statin drugs, lunasin can up regulate the expression of LDL-receptor gene. The contrasting effect of lunasin on these two SREBP-controlled genes can be explained by the selective recruitment of different co-regulatory transcription factors to two separate cholesterol-regulated promoters.

Lunasin's Effect On Expression Of Sp1 Coactivator

Figure 4:
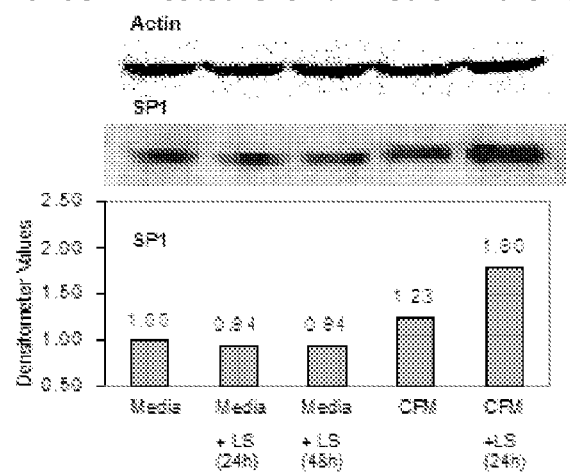
FIG. 4 shows the results of experiments measuring Sp1 expression in lunasin treated growth media and cholesterol free media.

Unlike HMG CoA-reductase, SREBP activation of LDL-receptor by sterol depletion requires increased recruitment of Sp1 co-activator to a site adjacent to SREBP in the promoter of LDL-receptor gene (25). As shown in FIG. 3, the up regulation of LDL-receptor by lunasin (LS) in cholesterol-free media may be due to increased availability and recruitment of the Sp1 coactivator to the LDL-receptor promoter. To test this hypothesis, the level of Sp1 has been determined in lunasin-treated growth media and cholesterol-free media by Western analysis using Sp1 antibody. FIG. 4 shows that Sp1 levels in control and lunasin-treated growth media were not significantly different. However, Sp1 levels increased in cholesterol-free media by 23%, compared to the growth media. The addition of lunasin in the cholesterol-free media further increased Sp1 levels by almost 60%, which closely mirrors the increase in LDL-receptor levels in lunasin-treated, cholesterol-free media.

The data from these experiments indicate that the increase in LDL-receptor expression by lunasin in sterol-depleted media could be attributed to the increased availability of the Sp1 transcriptional co-activator. Also, the inhibition of HMG-CoA reductase expression by lunasin lowers intracellular cholesterol levels that keeps SREBP activated, resulting in the upregulation of LDL receptor expression.

Therefore, the data shows that lunasin inhibits the expression of HMG-CoA reductase, the rate limiting enzyme in the body's metabolic pathway for synthesis of cholesterol and at the same time increases the expression of the LDL receptor, leading to increased clearance of low-density lipoprotein (LDL) from the bloodstream, which lowers total and LDL cholesterol in a mammal. Most circulating cholesterol in mammals is synthesized internally, typically 1000 mgs/day compared to 200-300 mgs/day from intestinal intake in a human diet. Thus the internal production of cholesterol as catalyzed by HMG Co-A reductase and the amount of LDL receptors in liver cell membranes are the most important factors in modulating cholesterol levels in mammals. Accordingly, these experiments demonstrate that an effective amount of lunasin reduces both LDL and total cholesterol levels in mammal.

Lunasin's Effect On Expression Of Sp1 Coactivator

Figure 5:
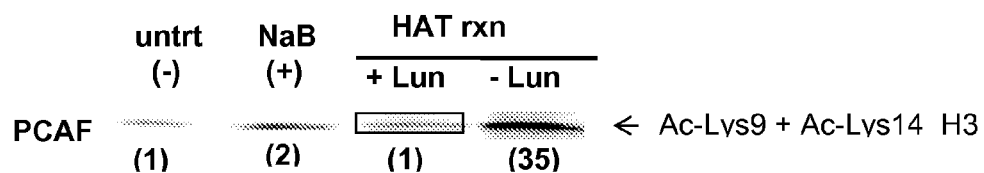
FIG. 5 shows the western blots from experiments on PCAF reaction products demonstrating that lunasin caused a dramatic reduction in histone H3 acetylation.

Inhibition of H3 histone acetylation by PCAF histone acetylase enzyme is required for the SREBP activation of genes involved in cholesterol biosynthesis including HMG CoA reductase (25). Previous study has shown that lunasin is a potent inhibitor of histone H3 acetylation in mammalian cells exposed to the histone deacetylase inhibitor, sodium butyrate (NaB) (20). To determine the effect of lunasin on histone H3 acetylation by PCAF, HAT assay reaction using acid-extracted histones from untreated HeLa cells as template was conducted. Immunoblotted reaction products have been stained with antibodies against diacetylated histone H3 (Ac-Lys9+Ac-Lys14) and the details of our experiment and its results are shown and described in FIG. 5. In brief, the HAT enzyme, PCAF, is shown to increase significantly histone H3 acetylation in the absence of lunasin (35-fold increase). However, the addition of lunasin in the PCAF reaction, resulted in dramatic reduction of histone H3 acetylation, indicating that lunasin is a potent inhibitor of histone H3 acetylation catalyzed by the PCAF acetylase enzyme.

Figure 6:
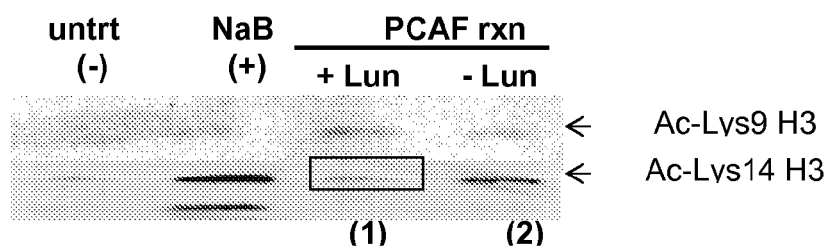
FIG. 6 shows the western blots from experiments on PCAF HAT reaction products demonstrating that lunasin caused a dramatic reduction in histone H3 acetylation

To determine the specific lysine residue in histone H3 that is inhibited by lunasin from being acetylated, immunoblotted products of PCAF acetylase reactions were hybridized with antibodies raised against acetylated Lys 9 and acetylated Lys 14 in H3 terminal tails. The results and details of our experiments, as shown and described in FIG. 6, demonstrate that lunasin specifically binds to Lys 14, preventing it from being acetylated by PCAF.

In one exemplary embodiment of the present invention, a method of inhibiting H3 acetylation in a mammal is provided. The method includes providing an effective amount of lunasin peptides to a mammal to inhibit H3 acetylation in the mammal.

In another exemplary embodiment of the present invention, a method of reducing expression of HMG CoA reductase in a mammal is provided. The method includes providing an effective amount of lunasin peptides to a mammal to reduce expression of HMG CoA reductase in the mammal.

In yet another exemplary embodiment of the present invention, a method of increasing LDL receptor expression in a mammal is provided. The method includes providing an effective amount of lunasin peptides to a mammal to increase LDL receptor expression in the mammal.

In yet another exemplary embodiment of the present invention, a method of increasing Sp1 transcriptional activator expression in a mammal is provided. The method includes providing an effective amount of lunasin peptides to a mammal to increase Sp1 transcriptional activator expression in the mammal.

In one aspect of at least on embodiment of the present invention, the effective amount of lunasin peptides that inhibit H3 acetylation, reduce expression of HMG CoA reductase, increase LDL receptor expression or increases Sp1 transcriptional activator expression in a mammal is 25 to 100 mgs daily. It should be appreciated that the effective amount of lunasin will depend, at least in part, on the size, weight, health and desired goals of the mammals consuming the compositions. Accordingly, it is believed that in at least one embodiment, the effective amount of lunasin provided to the mammal is 25 mg to 100 mg daily.

In another aspect of at least on embodiment of the present invention, the lunasin peptides include lunasin peptides or lunasin peptide derivatives. It should also be appreciated that the present invention includes the use of lunasin peptide derivatives, which are any peptides that contain the same functional units as lunasin. It should also be appreciated the products and compositions of the present invention can be used in, foods, powers, bars, capsules, shakes and other well known products consumed by mammals or used separately.

In yet another aspect of at least on embodiment of the present invention, the lunasin peptides are obtained from, soy, seed bearing plants other than soy, using recombinant DNA techniques and synthetic polypeptide production or any combination thereof.

In yet another aspect of at least one embodiment of the present invention, the method includes providing an effective amount of one or more protease enzyme inhibitors with or without the lunasin peptides. The protease enzyme inhibitors act to protect lunasin from digestion and facilitate absorption and delivery to the appropriate target areas. Examples of appropriate protease enzyme inhibitors include, but are not limited to, pancreatin, trypsin and/or chymotrypsin inhibitors. It should be appreciated that the scope of the present inventions includes the use of the lunasin and/or lunasin derivatives with any other composition or product that is known or believed to facilitate lunasin's absorption or delivery in a mammal.

While the products, compositions and related methods have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

REFERENCES

The numeric references incorporated above correspond to the following list of published papers and abstracts.
1. Adlercruz H & Mazur W. Phyto-oestrogens and Western diseases. *Ann. Med.* 29: 95-120 (1997).
2. Zhang X., Shu X O, Gao Y T, Yang G., Li Q, Li H, Jin F & Zheng W. Soy food consumption is associated with lower risk of coronary heart disease in Chinese women. *J. Nutr.* 133: 2874-2878 (2003).
3. Anderson J W, Johnstone B M & Cook-Newell M E. Meta-analysis of effects of soy protein intake on serum lipids in humans. *N Eng J Med* 333: 276-282 (1995).
4. Anthony M S, Clarkson T B, Hughes C L et al. Soybean isoflavones improve cardiovascular risk factors without affecting the reproductive system of peripubertal rhesus monkeys. *J Nutr* 126: 43-50 (1996).
5. Arjmandi B H, Khan D A, Juma S & Svanborg A. The ovarian hormone deficiency-induced hypercholesterolomia is reversed by soy protein and the synthetic isoflavone, ipriflavone. *Nutr. Res.* 17: 885-894 (1997).
6. Kirk E A, Sutherland P, Wang S A. Dietary isoflavones reduce plasma cholesterol and atherosclerosis in C57BL/6 mice but not LDL-receptor deficient mice. *J. Nutr.* 128: 954-959 (1998).
7. Crouse J R, Morgan T, Terry J G. A randomizing trial comparing the effect of casein with that of soy protein containing varying amounts of isoflavones on plasma concentrations of lipids and lipoproteins. *Arch Intern Med.* 159: 2070-2076 (1999).
8. Wong W W, Smith E O, Stuff J E. Cholesterol lowering effect of soy protein in normocholesterolomic and hypercholesterolomic men. *Am J Clin Nutr* 68: 1385S-1389S (1998).
9. Greaves K A, Parks J S, Williams J K & Wagner J D. Intact dietary soy protein, but not adding an isoflavone-rich soy extract to casein, improves plasma lipids in ovariectomized cynomolgus monkeys. *J Nutr* 129: 1585-1592 (1999).
10. Verrillo A, Teresa de A, Giarrusso P C. Soybean protein diets in the management of type II hyperlipoproteinaemia. *Atherosclerosis,* 54: 321 (1985).
11. Kris-Etherton P & West S G. Soy protein with or without isoflavones: in search of a cardioprotective mechanism of action. *Am J Clin Nutr* 81: 5-6 (2005).
12. Anthony M S. Phytoestrogens and cardiovascular disease: Where's the meat? *Arterioscler Thromb Vasc Biol* 22: 1245-1257 (2002).
13. Vega-Lopez S, Yeum K-J, Leckler J L. Plasma antioxidant capacity in response to diets high in soy or animal protein with or without isoflavones. *Am J Clin Nutr* 81: 43-49 (2005).
14. Oakenfull D G & Sidhu G S. Could saponins be a useful treatment for hypercholesterolaemia? *Eur J Clin Nutr* 44: 79-88 (1990).
15. Adams M R, Golden D L, Franke A A, Potter S M, Smith H S & Anthony M S. Dietary soy beta-conglycinin (7S globulin) inhibits atherosclerosis in mice. *J. Nutr.* 134: 511-516 (2004).
16. Sacks F M, Lichtenstein A., Van Horn L., Harris W., Kris-Etherton P. & Winston M. Soy protein, isoflavones and cardiovascular health. An American Heart Association Science Advisory for Professionals from the Nutrition Committee. Circulation. On-line publication, Feb. 21, 2006.
17. Galvez, A. F., Revilleza, M. J. R. & de Lumen, B. O. A novel methionine-rich protein from soybean cotyledon: cloning and characterization of cDNA. *Plant Physiol* 114: 1567 (1997).
18. Galvez, A. F. & de Lumen, B. O. A soybean cDNA encoding a chromatin-binding peptide inhibits mitosis of mammalian cells. *Nature Biotech.* 17: 495-500 (1999).
19. de Mejia E G, Vasconez M., de Lumen B O & Nelson R. Lunasin concentration in different soybean genotypes, commercial soy protein and isoflavone products. *J Agric Food Chem* 52: 5882-5887 (2004).
20. Galvez, A. F. Chen, N., Macasieb, J., & de Lumen, B. O. Chemopreventive property of a soybean peptide. *Cancer Res.* 61: 7473-7478 (2001).
21. De Pinho, R. A. The cancer-chromatin connection. *Nature* 391: 533-536 (1998).
22. Kuzmin I & Geil L. DNA methylation and chromatin modifications in cancer and development. *Int Arch Biosci* 2001: 1047-1056 (2001).
23. Magbanua M, Dawson K, Huang L, Malyj W, Gregg J, Galvez A & Rodriguez R L. Nutrient—Gene Interactions Involving Soy Peptide and *Chemopreventive Genes in Prostate Epithelial Cells,* in *Nutritional Genomics—Discovering the Path to Personalized Nutrition,* J. Kaput and R. L. Rodriguez eds., Wiley and Sons, New Jersey (2005).
24. Bennett M K & Osborne T F. Nutrient regulation of gene expression by the sterol regulatory element binding proteins: Increased recruitment of gene-specific coregulatory factors and selective hyperacetylation of histone H3 in vivo. *PNAS* 97: 6340-6344 (2000).
25. Brown M S & Goldstein J L. Lowering plasma cholesterol by raising LDL receptors. *Atherosclerosis Suppl* 5: 57-59 (2004).
26. Sirtori C R, Gatti E, Mantero O, Conti F., et al. Clinical experience with the soybean protein diet in the treatment of hypercholesterolemia. *Am J Clin Nutr.* 32: 1645-1658 (1979).
27. Descovich G C, Ceredi C., Gaddi A., Benassi M S, et al., Multicentre study of soybean protein diet for outpatient hyper-cholesterolaemic patients. *Lancet* 2: 709-712 (1980).
28. Lam, Y., Galvez, A., and de Lumen, B. O. Lunasin suppresses E1A-mediated transformation of mammalian cells but does not inhibit growth of immortalized and established cancer cell lines. *Nutrition & Cancer,* 47: 88-94 (2003).
29. Coqueret, O. New roles for p21 and p27 cell-cycle inhibitors: A function for each cell compartment? *Trends in Cell Biology,* 13: 65-70, (2003).
30. Bruzzone, R., White, T. W., and Paul, D. L. Connections with connexins: The molecular basis of direct intercellular signaling. *European Journal of Biochemistry,* 238: 1-27 (1996).
31. Mullen E, Brown R M, Osborne T F & Shay N F. Soy isoflavones affect sterol regulatory element binding proteins (SREBPs) and SREBP-regulated genes in HepG2 cells. *J. Nutr.* 134: 2942-2947 (2004).
32. Gherardi E., Thomas K, Le Cras T D, Fitzsimmons C, Moorby C D & Bowyer D E. Growth requirements and expression of LDL receptor and HMG CoA-reductase in HepG2 hepatoblastoma cells cultured in a chemically defined medium. *J Cell Sci.* 103: 531-539 (1992).

I claim:

1. A method of inhibiting histone H3 acetylation by PCAF in a mammal, the method comprising:
providing an effective amount of a peptide comprising SEQUENCE ID NO: 2 to a mammal to inhibit PCAF from acetylating histone H3 in the mammal.

2. A method of claim 1, wherein the effective amount of the peptide is 25 to 100 mgs daily.

3. A method of claim 1, wherein the peptide is obtained from one or more of the following groups: soy, seed bearing plants other than soy, using recombinant DNA techniques and synthetic polypeptide production.

4. A method of claim 1, further comprising:
providing an effective amount of one or more protease enzyme inhibitors.

5. A method of reducing expression of HMG CoA reductase in a mammal, the method comprising:
providing an effective amount of a peptide comprising SEQUENCE ID NO: 2 to a mammal to reduce expression of HMG CoA reductase in the mammal.

6. A method of claim 5, wherein the effective amount of the peptide is 25 to 100 mgs daily.

7. A method of claim 5, wherein the peptide is obtained from one or more of the following groups: soy, seed bearing plants other than soy, using recombinant DNA techniques and synthetic polypeptide production.

8. A method of claim 5, further comprising:
providing an effective amount of one or more protease enzyme inhibitors.

9. A method of increasing LDL receptor expression in a mammal, the method comprising:

providing an effective amount of a peptide comprising SEQUENCE ID NO: 2 to a mammal to increase LDL receptor expression in the mammal.

10. A method of claim 9, wherein the effective amount of the peptide is 25 to 100 mgs daily.

11. A method of claim 9, wherein the peptide is obtained from one or more of the following groups: soy, seed bearing plants other than soy, using recombinant DNA techniques and synthetic polypeptide production.

12. A method of claim 9, further comprising:

providing an effective amount of one or more protease enzyme inhibitors.

13. A method of increasing Sp 1 transcriptional activator expression in a mammal, the method comprising:

providing an effective amount of a peptide comprising SEQUENCE ID NO:2 to a mammal to increase Sp1 transcriptional activator expression in the mammal.

14. A method of claim 13, wherein the effective amount of the peptide is 25 to 100 mgs daily.

15. A method of claim 13, wherein the peptide is obtained from one or more of the following groups: soy, seed bearing plants other than soy, using recombinant DNA techniques and synthetic polypeptide production.

16. A method of claim 13, further comprising:

providing an effective amount of one or more protease enzyme inhibitors.

\* \* \* \* \*